US006939512B2

United States Patent
Lihl et al.

(10) Patent No.: US 6,939,512 B2
(45) Date of Patent: *Sep. 6, 2005

(54) HEATING AND COOLING DEVICE FOR AN APPARATUS FOR TISSUE PROCESSING FOR THE TISSUE EMBEDDING

(75) Inventors: Reinhard Lihl, Vienna (AT); Michael Zimmerman, Leopoldsdorf (AT); Guenther Bock, Vienna (AT); Ian Lamswood, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 492 days.

This patent is subject to a terminal disclaimer.

(21) Appl. No.: 10/100,848

(22) Filed: Mar. 18, 2002

(65) Prior Publication Data

US 2003/0017080 A1 Jan. 23, 2003

(30) Foreign Application Priority Data

Mar. 22, 2001 (EP) ............................................. 01107131

(51) Int. Cl.$^7$ .............................................. G01N 25/20
(52) U.S. Cl. ........................ 422/67; 422/102; 436/147; 436/174; 436/176; 118/66; 118/421

(58) Field of Search .................................. 422/102–104, 422/64, 67; 436/43, 174, 176, 147, 155, 157; 118/66, 421, 501, 704

(56) References Cited

U.S. PATENT DOCUMENTS

| 3,807,353 A | * | 4/1974 | Kobernick | .................. 118/702 |
| 4,530,304 A | * | 7/1985 | Gardos | ........................ 118/66 |
| 4,688,517 A | | 8/1987 | Hollman | |
| 5,582,796 A | * | 12/1996 | Carey et al. | ................... 422/65 |

* cited by examiner

Primary Examiner—Lyle A. Alexander
(74) Attorney, Agent, or Firm—Simpson & Simpson, PLLC

(57) ABSTRACT

A heating and cooling device (3) for an apparatus (1) for tissue preparation for the tissue embedding is disclosed. The apparatus (1) has a free space (13) for the accommodation of a transport plate (15). The apparatus (1) is surrounded by a housing (5) which defines an upper side (8) and a heating and cooling device (3) that is provided on the upper side (8) of the housing (5), and the heating and cooling device (3) has a reception (23) with at least one chamber (32) for the accommodation of at least one processing container (17). The heating and cooling device (3) is pivotable with respect to the upper side (8) of the housing (5).

4 Claims, 3 Drawing Sheets

HEATING AND COOLING DEVICE FOR AN APPARATUS FOR TISSUE PROCESSING FOR THE TISSUE EMBEDDING

CROSS REFERENCE TO RELATED APPLICATIONS

This invention claims priority of the European patent application 01 107 131.3, filed Mar. 22, 2001, which is incorporated by reference herein.

FIELD OF THE INVENTION

The invention concerns a heating and cooling device for an apparatus for tissue processing for the tissue preparation.

BACKGROUND OF THE INVENTION

The U.S. Pat. No. 4,688,517 discloses an apparatus for processing tissue samples. On a rotatable table a plurality of processing containers are provided for the sample processing. The table is rotatable so that the processing containers can be transported to a processing station at which the tissue samples are successively immersed in different processing liquids. For a suitable tempering of the actually used processing liquids a heating and cooling device is permanently mounted to the housing of the apparatus. Since the heating and cooling device extends into the area of the table, it is extremely inconvenient and requires a plurality of manipulation steps to exchange the rotatable table.

SUMMARY OF THE INVENTION

It is the object of the invention to provide a heating and cooling device for an apparatus for tissue processing for the tissue preparation which enables a simple and variable usage of the apparatus.

The object above is solved by a heating and cooling device for an apparatus for tissue preparation for the tissue embedding, which comprises: a reception with at least one chamber for the accommodation of at least one processing container wherein the heating and cooling device is pivotable with respect to a housing of the apparatus.

The possibility to pivot the heating and cooling device is achieved in one embodiment in that the heating and cooling device is pivotable around an axis which is parallel to the upper side of the housing. Moreover, the heating and cooling device is pivotable around an axis which is perpendicular to the upper side of the housing.

It is a further advantage of the invention to provide a heating and cooling device which is easily to exchange, so that the user can switch in a simple way between processing containers of different size. This is advantageous, when large tissue pieces need to be processed for the tissue embedding. In addition, the possibility to pivot the heating and cooling device simplifies the change of the transport plate extremely. Thus the heating and cooling device is lifted straight out of the free space of the housing. It is not necessary to remove some processing containers are removed from the transport plate in order to enable the change of the transport plate. The change of the heating and cooling device can be done in a very simple way. To do so, the pins are to be removed from the hinges and subsequently the whole heating and cooling device is lifted off. A coding is transmitted to a control device in the housing which accordingly coordinates the rotation and lift movements of the transport plate. In the different heating and cooling devices the accommodation for the processing containers are designed in different sizes and each connected permanently to a power supply for the heating and cooling device. In an embodiment the accommodation for the processing containers is designed so that a first and a second chamber for the processing containers are provided, wherein the second chamber is provided with a protective cover. The first chamber serves for tempering of the processing liquids in the processing container and for dipping the tissue sample into the processing container. The second chamber can be used for preheating the processing liquid in the processing container. The protective cover eliminates an unnecessary evaporation of the processing liquid.

BRIEF DESCRIPTION OF THE DRAWINGS

In the drawing the invention is schematically shown and described on the basis of the figures below. The figures show in.

DETAILED DESCRIPTION OF THE INVENTION

Figure 1:
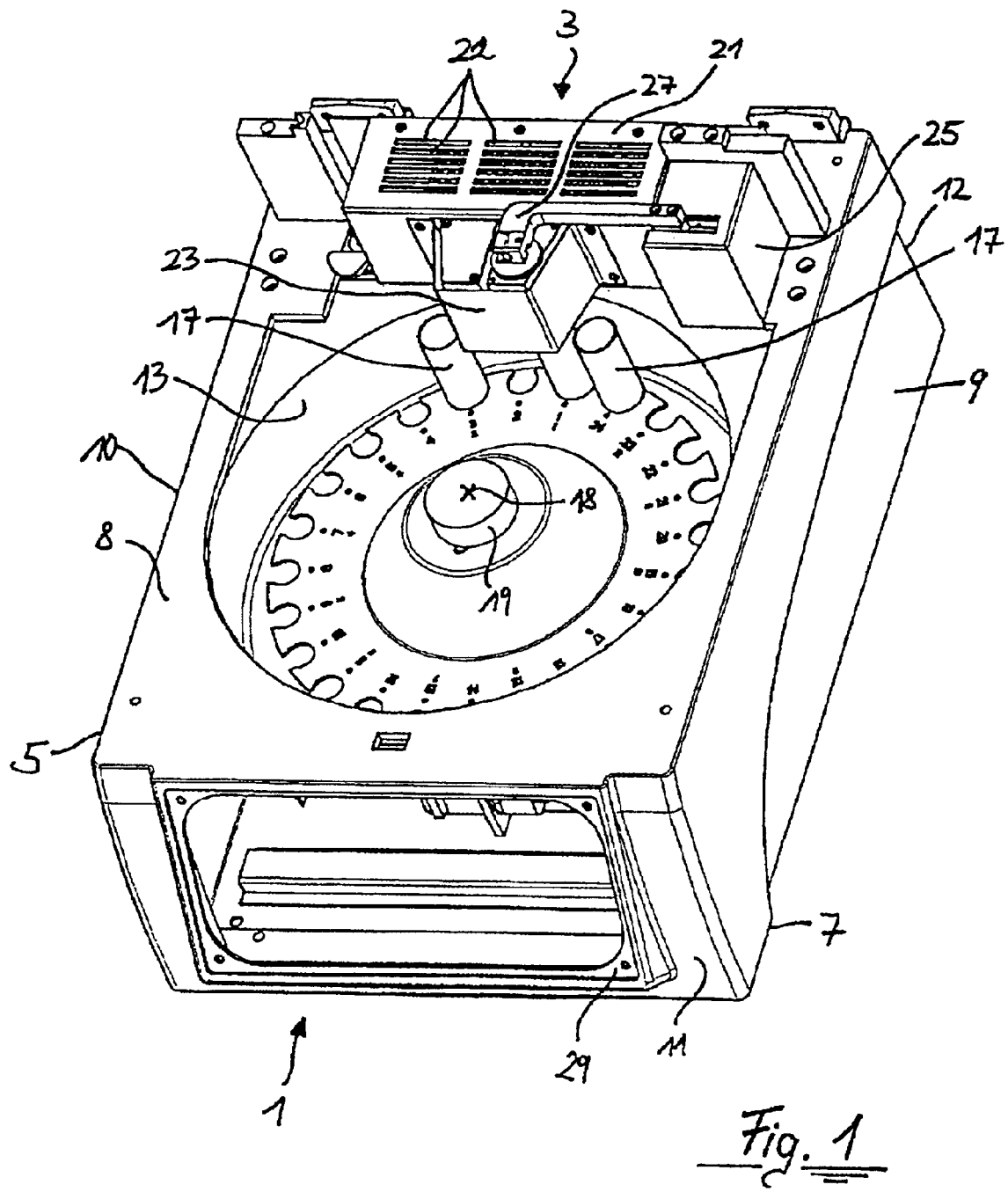
FIG. 1 a perspective view of the apparatus for tissue preparation for the tissue embedding.

The apparatus 1 for tissue preparation for the tissue embedding is shown in FIG. 1 together with a heating and cooling device 3 in a perspective view. The apparatus 1 for tissue preparation for the tissue embedding consists of a housing 5 which essentially encloses mechanical and electronic parts (not represented in FIG. 1) of the apparatus 1. The housing 5 comprises an under side 7, an upper side 8, a right and a left side wall 9 and 10 and a front and a back side 11 and 12. In the upper side 8 of the housing 5 a free space 13 is provided by which the access to the inside of the apparatus 1 is enabled. By the free space 13 access to the transport plate 15, that is arranged inside the housing 5, is possible. The transport plate 15 is configured in this embodiment in a circular shaped manner and possesses at its edge a plurality of cut outs 16 which serve for the accommodation of processing containers 17. The transport plate 15 is freely rotatable around an axle 18 and can be raised and lowered additionally in the direction of the axle 18. The transport plate 15 is secured by means of a securing element 19. The heating and cooling device 3 comprises a power supply 21 which is provided with several vent openings 22 for venting off the produced heat. To the power supply 21 a reception 23 for the processing containers 17 is attached and arranged in such a manner that it projects at least partly into the area of the free space 13. As mentioned already above the transport plate 15 can be raised and lowered in the direction of the axle 18. In the raised status at least one processing container 17 is in the reception 23 and can be kept at a specific temperature in an appropriate way. The processing containers 17 contain different liquids which are necessary for the processing of the tissue samples. Beside the heating and cooling device 3 a mechanic 25 is provided to which an arm 27 is connected. At the arm 27 a tissue sample (not shown) is attached which is submitted to an appropriate sample processing program. The arm 27 can move up and down, whereby the tissue sample is dipped into the liquid, which is in the processing container 17 being in the reception 23 at the moment.

The front side 11 of the housing 5 has an approximately rectangular cut out 29, into which a control element (not shown) for the user can be placed. From the control element the user is able to recall or design various processing programs.

Figure 2:
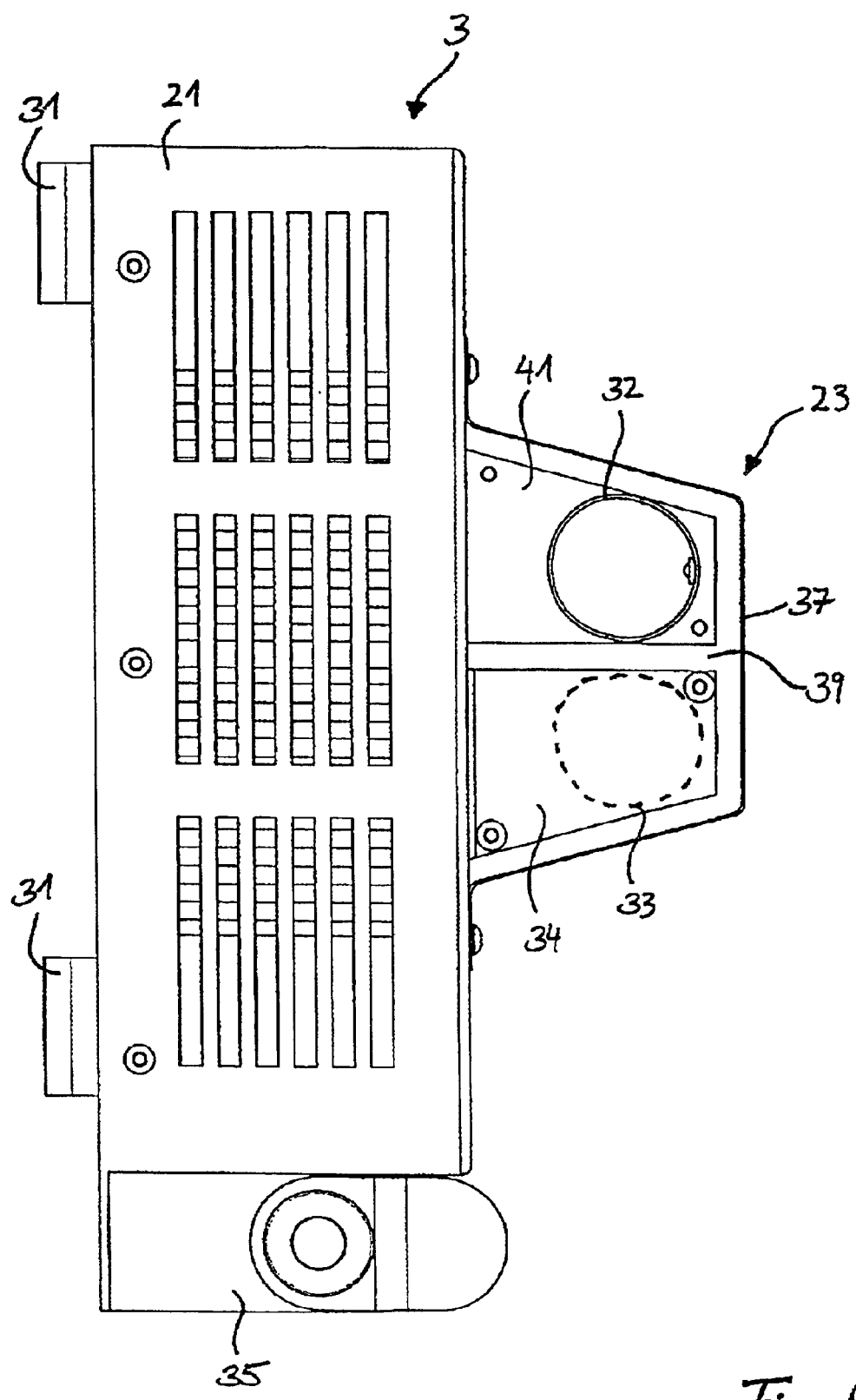
FIG. 2 a plan view of a first embodiment of a heating and cooling device.

FIG. 2 shows a first embodiment of the heating and cooling device 3. The heating and cooling device 3 comprises a power supply 21 and a reception 23 for the processing containers 17. At least one hinge 31 is provided at the side of the power supply 21 which is opposite to the reception 23 for the processing containers 17. In the embodiment shown here two hinges 31 are provided. With the hinges 31 the entire heating and cooling device 3 can be pivoted away from the upper side 8 of the housing 5. Thus the area above the free space 13 becomes free from obstacles, and the transport plate 15 can be taken out of the housing 5 in a simple manner. In addition, the hinges 31 can be loosened in a simple manner in order to thus quickly exchange the heating and cooling device 3 against another embodiment of the heating and cooling device 3 (see FIG. 3). The reception 23 for the processing containers 17 is provided opposite to the side of the power supply 21 at which the hinges 31 are mounted. In the embodiment shown in FIG. 2, the reception 23 is divided into a first and a second chamber 32 and 33. The first chamber 32 is of cylindrical form and open at the top and at the bottom. The processing container 17 can be introduced from the bottom and from above the arm 27 with the tissue sample can dip into the processing liquid. The second chamber 33 (not shown) is of cylindrical form as well and closed at the top with a plate 34. The second chamber 33 serves for preheating or pre-cooling the processing liquids in a processing container 17. The plate 34 thus prevents an evaporation of the processing liquids.

To the power supply 21 a latch 35 is fastened as well which connects the heating and cooling device 3 with the housing 5 in the working position. To do so, an interlock (not shown) is provided at the housing 5 which serves for a safe positioning of the heating and cooling device 3 with respect to the housing 5. This connection which can be made easily is important on the one hand in order to change the heating and cooling device 3 fast and on the other hand to achieve a fixed and unchangeable position of the heating and cooling device 3 with respect to the housing 5. The fixed and unchangeable position is necessary in order to ensure that the processing containers 17 can be inserted into the first and second chamber 32 and 33 without cant.

The reception 23 has a protective cover 37 which protects the user against possible burnings. In addition, the protective cover 37 is equipped with an isolation layer 39 which separates the first chamber 32 from the second chamber 33. In a block 41 of a good heat conducting material the first and the second chamber 32 and 33 are configured.

Figure 3:
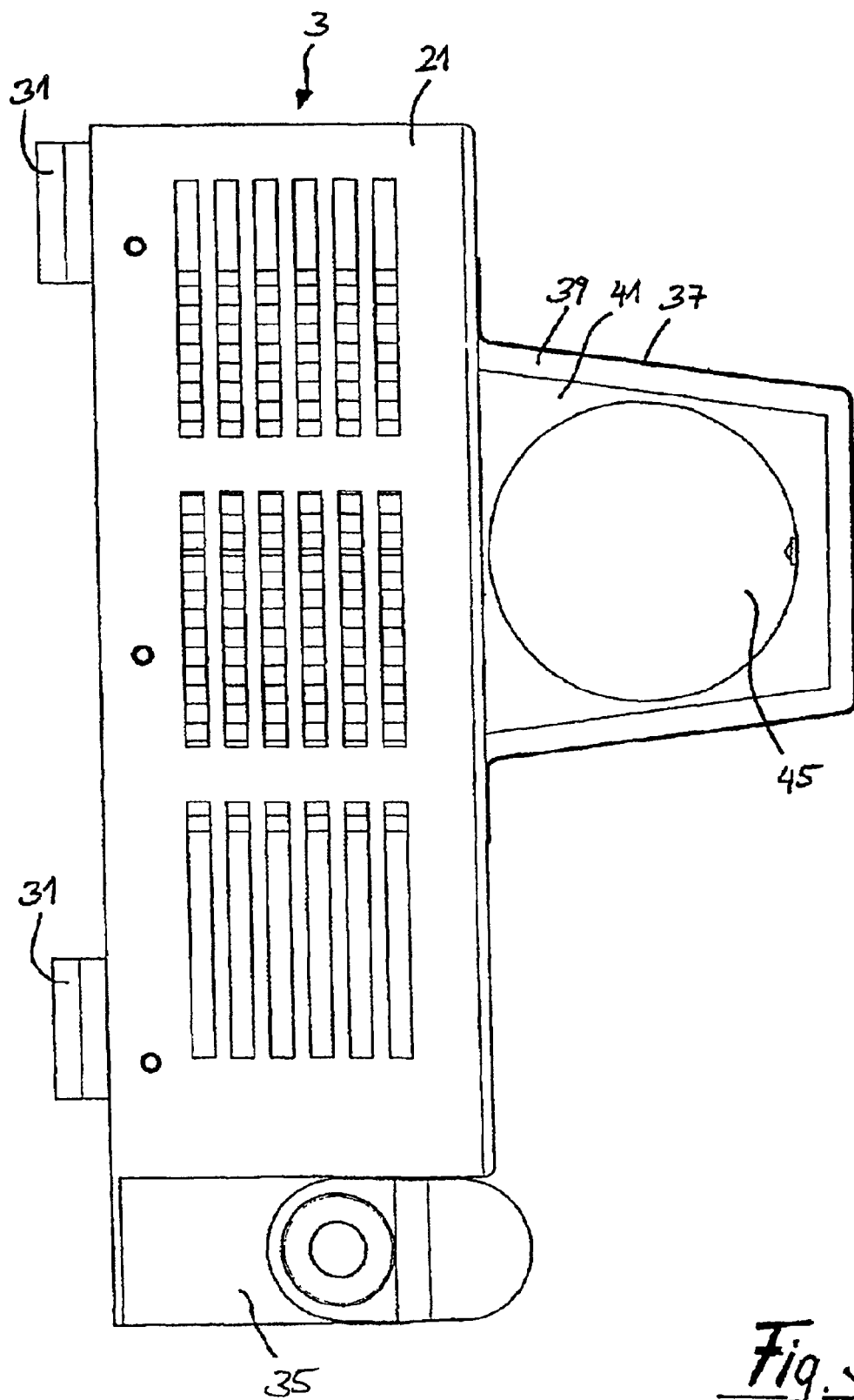
FIG. 3 a plan view of a second embodiment of a heating and cooling device.

FIG. 3 shows a further embodiment of the invention, wherein for the sake of simplicity for elements identical with elements in FIG. 2 the same reference numerals are used. The difference to the embodiment as shown in FIG. 2 is, that the reception 23 has only one chamber 45. The chamber 45 has a diameter which is greater than the diameter of the first and the second chamber 32 and 33 as shown in the embodiment of FIG. 2. Onto the transport plate 15 processing containers 17 can be attached which differ in diameter. A coding (not shown) is provided which communicates to the control unit in the housing 5 how the transport plate 15 has to be controlled with respect to the used heating and cooling device 3. The coding can be done for example by the contacts of the electric plug, other electric connections, a barcode or an other coding. As already mentioned in the description of FIG. 2 the heating and cooling device 3 can be exchanged. In order to achieve a fast and simple removal pins (not shown) are provided in the hinges 31. After the removal of the pins the heating and cooling device 3 can be removed and exchanged against another one.

The invention was described with respect to a specific embodiment of the invention form. It is however obvious that changes and modifications can be carried out without leaving the scope of protection of the claims below.

PARTS LIST 1 apparatus
3 heating and cooling device
5 housing
6 cover
7 under side
8 upper side
9 right side wall
10 left side wall
11 frontside
12 back side
13 free space
15 transport plate
16 cut out
17 processing containers
18 axle
19 securing element
21 power supply
22 vent opening
23 reception
25 mechanic
27 arm
29 cut out
31 hinge
32 first chamber
33 second chamber
34 plate
35 latch
37 protective cover
39 isolation layer
41 block
45 chamber

What is claimed is:

1. A heating and cooling device for an apparatus for tissue preparation for the tissue embedding, comprising:
    a free space for the accommodation of a transport plate that is surrounded by a housing; and,
    a reception with at least one chamber for the accommodation of at least one processing container wherein the heating and cooling device is pivotable to one position with respect to the housing of the apparatus, so that the area above the free space becomes free from obstacles and the transport plate can be taken out of the housing, and wherein the heating and cooling device is pivotable to another position in the housing so that the heating and cooling device can heat or cool the tissue preparation, and
    wherein at least one hinge is provided at the heating and cooling device at the side which faces away from the reception for the processing containers.

2. The heating and cooling device as defined in claim 1 further comprising an axis parallel to the upper side of the housing, wherein said at least one hinge is pivotable around said axis.

3. The heating and cooling device as defined in claim 1, further comprising an axis perpendicular to the upper side of the housing, wherein said at least one hinge is pivotable around said axis.

4. The heating and cooling device as defined in claim 1, wherein said at least one hinge (32) is configured releasable.

* * * * *